United States Patent
Zhao et al.

(10) Patent No.: US 12,281,300 B2
(45) Date of Patent: *Apr. 22, 2025

(54) SYSTEMS AND METHODS FOR BLEACHING MICROBIAL CELLS

(71) Applicant: GW Nutrition Inc., Slater, IA (US)

(72) Inventors: Xuefei Zhao, Ames, IA (US); Zhiyou Wen, Ames, IA (US); Martin Anthony Gross, Ames, IA (US); Everett Donald Dudley, Jr., Highland Park, IL (US)

(73) Assignee: GW Nutrition Inc., Slater, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/674,050

(22) Filed: May 24, 2024

(65) Prior Publication Data
US 2024/0309354 A1     Sep. 19, 2024

Related U.S. Application Data

(63) Continuation of application No. 17/369,421, filed on Jul. 7, 2021, now Pat. No. 12,077,751.

(60) Provisional application No. 63/048,691, filed on Jul. 7, 2020.

(51) Int. Cl.
| | |
|---|---|
| C12N 13/00 | (2006.01) |
| A23B 2/53 | (2025.01) |
| A23K 10/12 | (2016.01) |
| A23L 17/60 | (2016.01) |
| C12M 1/00 | (2006.01) |
| C12N 1/12 | (2006.01) |

(52) U.S. Cl.
CPC ............ *C12N 13/00* (2013.01); *A23B 2/53* (2025.01); *A23K 10/12* (2016.05); *A23L 17/60* (2016.08); *C12M 23/18* (2013.01); *C12N 1/12* (2013.01); *A23V 2002/00* (2013.01)

(58) Field of Classification Search
CPC ......... C12N 13/00; A23K 10/12; A23L 17/60; A23L 3/28
See application file for complete search history.

(56) References Cited

U.S. PATENT DOCUMENTS

| | | | | |
|---|---|---|---|---|
| 3,197,309 | A * | 7/1965 | Chapman | A23L 17/60 435/946 |
| 8,940,520 | B2 * | 1/2015 | Martin | C12N 1/12 435/257.1 |

(Continued)

OTHER PUBLICATIONS

Döhler, Günter. "Effect of UV-B radiation on biomass production, pigmentation and protein content of marine diatoms." *Zeitschrift für Naturforschung C* 39.6 (1984): 634-638.

(Continued)

*Primary Examiner* — Stephanie A Cox
(74) *Attorney, Agent, or Firm* — Frost Brown Todd LLP; Vance V. VanDrake, III; Alexander J. Johnson

(57) ABSTRACT

A method of treating microbial biomass includes mixing the microbial biomass in a liquid to form a suspension, the microbial biomass having an initial color, and exposing the suspension to light to form treated microbial biomass, the treated microbial biomass having a treated color. The treated color is lighter than the initial color. The microbial biomass can also have an initial taste and odor that are stronger than a treated taste and odor of the treated microbial biomass.

20 Claims, 4 Drawing Sheets

(56) References Cited

U.S. PATENT DOCUMENTS

| | | | | |
|---|---|---|---|---|
| 2010/0210001 | A1* | 8/2010 | Seyfried | C12N 13/00 435/257.1 |
| 2011/0287526 | A1* | 11/2011 | Martin | C12N 1/12 435/257.1 |
| 2013/0266556 | A9* | 10/2013 | Medoff | C12P 19/44 426/624 |
| 2014/0127776 | A1* | 5/2014 | Picard | C12M 23/48 435/178 |
| 2019/0254291 | A1* | 8/2019 | Brooks | A23K 10/16 |
| 2022/0273007 | A1* | 9/2022 | Hokari | A23L 17/60 |
| 2022/0400719 | A1* | 12/2022 | Agoda-Tandjawa | A23L 17/60 |
| 2022/0413166 | A1* | 12/2022 | Saccomanno | A23B 7/015 |
| 2024/0080950 | A1* | 3/2024 | Frederixon | H05B 6/78 |

OTHER PUBLICATIONS

Singh, Umesb, et al. "Mass production of Pleurotus eryngii mycelia under submerged culture conditions with improved minerals and vitamin D2." *Lwt* 131 (2020): 109665.

\* cited by examiner

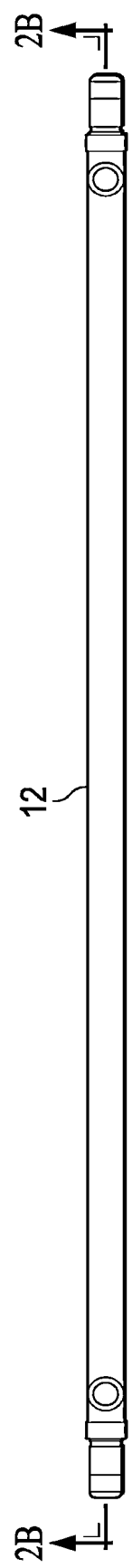

SYSTEMS AND METHODS FOR BLEACHING MICROBIAL CELLS

REFERENCE TO RELATED APPLICATIONS

The present application is a continuation of U.S. patent application Ser. No. 17/369,421, filed Jul. 7, 2021, which claims the priority benefit of U.S. Provisional Patent Application No. 63/048,691, filed Jul. 7, 2020, wherein the contents of each are hereby incorporated by reference in their entirety.

TECHNICAL FIELD

Embodiments of the technology relate, in general, to microbial technology, and in particular, to systems and methods for physically bleaching microbial cells.

BACKGROUND

Certain types of algae are used as food sources. However, commercially available algal powders have a deep green color and a strong odor and taste. There is a need for improved algal powders.

BRIEF DESCRIPTION OF THE DRAWINGS

The present disclosure will be more readily understood from a detailed description of some example embodiments taken in conjunction with the following figures:

FIGS. 2A and 2B depict an example system allowing flow of a suspension concentrically around a light source according to an embodiment.

DETAILED DESCRIPTION

Figure 1:
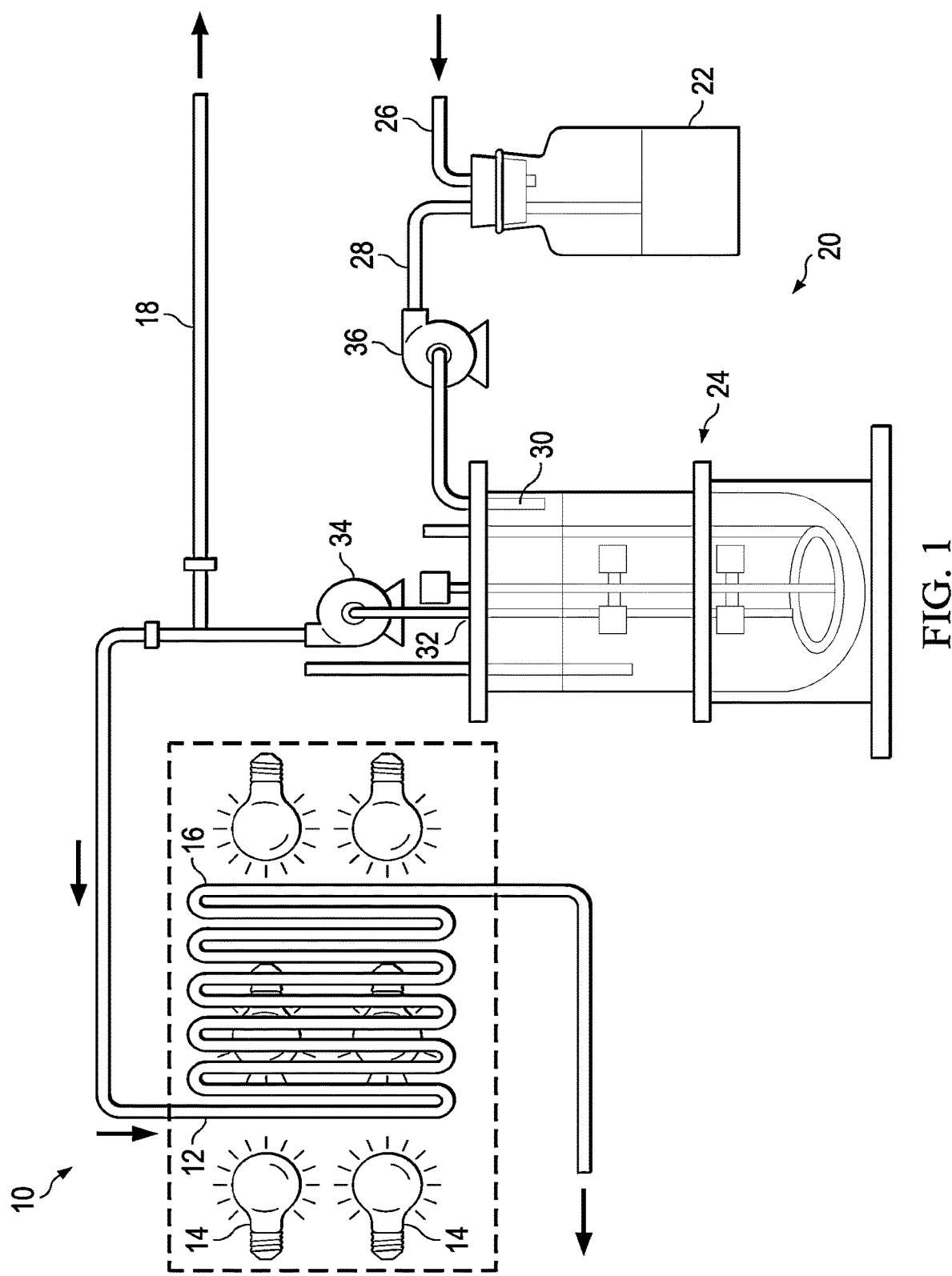
FIG. 1 depicts a schematic view of a treatment system and growth system according to an embodiment.

Various non-limiting embodiments of the present disclosure will now be described to provide an overall understanding of the principles of the structure, function, and use of the systems and processes disclosed herein. One or more examples of these non-limiting embodiments are illustrated in the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment." "some example embodiments," "one example embodiment," or "in an embodiment" in places throughout the specification are not necessarily all referring to the same embodiment. Furthermore, the particular features, structures or characteristics may be combined in any suitable manner in one or more embodiments.

Described herein are example embodiments of actively bleaching microbial biomass, such as algae or other types of biomass. In an embodiment where the microbial biomass is microalgae biomass, the bleached microalgae may be rich in protein. In some embodiments, systems and methods can be used to produce algae for food production, animal feed production and other food or feed supplement use.

In one example embodiment, non-chemical systems and methods can provide bleached material or biomass with reduced color, flavor, or odor. Because the bleaching process can be environmental, light based, or otherwise non-chemical, no potentially harmful bleaching chemicals are used in at least one embodiment. For example, a chemical bleaching agent may not be directly added to cause the bleaching; however, chemical reactions may occur naturally within the biomass due to the external or environment-based active bleaching process. It will be appreciated that various non-chemical or physical systems and methods can be combined with chemical techniques as appropriate for different applications.

The examples discussed herein are examples only and are provided to assist in the explanation of the apparatuses, devices, systems, and methods described herein. None of the features or components shown in the drawings or discussed below should be taken as mandatory for any specific implementation of any of the apparatuses, devices, systems, or methods unless specifically designated as mandatory. For case of reading and clarity, certain components, modules, or methods may be described solely in connection with a specific figure. Any failure to specifically describe a combination or sub-combination of components should not be understood as an indication that any combination or sub-combination is not possible. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

Example embodiments described herein can minimize or eliminate the use of harsh bleaching chemicals while delivering high value bio-based products from microbial biomass. Example embodiments can play a beneficial role in creating a system that can economically produce bleached microbial biomass for food production, animal feed production, food, or feed supplement use, or for any other suitable purpose. Additionally, embodiments described herein may result in bleached microbial biomass without the need for adding heat, adding absorbents that may require an alkaline suspension liquid, or suppressing the generation of carbon dioxide.

Example embodiments can include an algal growth system or mechanized harvesting system, which can remove concentrated algae in-situ from an attachment material and can minimize the amount of de watering needed post-harvest.

Referring to FIG. 1, an example embodiment of a treatment system 10 is disclosed. The microbial biomass may be mixed in a liquid to form a suspension. Suitable examples of the liquid include, without limitation, water, a microbial growth medium, or a microbial growth broth. The concentration of the microbial biomass in the liquid may vary. In some embodiments, the concentration may be in a range of greater than 0.01 to 100 grams of dry biomass per liter of liquid, or greater than 0 g/L to 10 g/L, or greater than 5 g/L to 9 g/L. In an embodiment, the pressure can be at ambient pressure. The suspension is directed through one or more tubes 12, which are exposed to one or more artificial lights 14. As the suspension passes through the tubes 12, the energy from the lights 14 bleaches the microbial biomass. For example, the energy from the lights 14 may degrade chlorophyll present in the microbial biomass. In various embodiments, the energy from the lights 14 harms, kills, or lyses the microbial cells. Lysing the microbial cells can provide benefits to the treated biomass. For example, whole cell algae is difficult or impossible for humans or animals to digest. Lysing the cells of algal biomass may allow the treated biomass to be more easily digestible by humans or animals. In an embodiment where cells of the biomass are not lysed, the treated biomass may be processed to crack, break, or disrupt the cells in the treated biomass.

As shown, a serial design is contemplated, which may be a simple and cost-efficient design because such a system may minimize the amount of wasted space and may maximize the amount of biomass bleached in a small area. The tubes 12 are arranged in a series with connectors 16 fluidically coupling each of the tubes 12. However, other embodiments can include any configuration that includes a light being directed at the microbial biomass. In an embodiment, the tubes 12 may surround the lights 14. For example, as shown in FIGS. 2A and 2B, a light 14 may be concentric with a tube 12 where the suspension surrounds the light 14. An example of a concentric tube system includes the IL-TF-5000-1 from Glasco UV. Such a configuration can be beneficial in maximizing the amount of light exposed to the microbial biomass. The treated biomass can then be separated from the suspension. It will be appreciated that the treated biomass can be separated using a variety of techniques, such as via a filter or centrifuge. The separated treated biomass can then be dried. The dried treated biomass can then be packaged.

The size or diameter of the tubes 12 and the flow rate may vary. For example, the tube diameter may be in a range of 0.1 to 100 cm, or the tube diameter may be larger. The size of the tubes 12 may be determined based on a ratio of surface area of exposure to the working volume. The tubes 12 may be transparent or translucent and can be made of, for example, glass. The tubes 12, and any associated components, can be movable or removable for cleaning, replacement, adjustment, or the like. It will be appreciated that such movement can be manual or can be automated if desirable. Additionally, the flow rate of the suspension through the tubes 12 can vary. In some embodiments, the flow rate can be in a range of 0.1 L/min to 10,000 L/min. It will be appreciated that the flow rate and configuration of the tubes 12 may be determined based on the desired time that the microbial biomass is exposed to the light.

In an embodiment, the treatment system 10 may include a line 18 for taking samples. A sample may be analyzed to determine the progress of the treatment, as discussed further below.

In some embodiments, the suspension may be subjected to turbulent flow as it moves past the light. For example, turbulent flow can be created by increasing the fluid velocity through the tube. In an embodiment, turbulent flow may have a Reynolds number of greater than 4,000. Turbulent flow may be created, in various embodiments, by increasing the cell suspension flow rate, decreasing the tube diameter, increasing the flow velocity, increasing the cell suspension density, decreasing the cell suspension kinematic viscosity, or a combination thereof.

The wavelength of the light may vary. In an embodiment, the light may be full spectrum light. In some embodiments, the wavelength of the light may be in the UV range (e.g., excluding non-UV range wavelengths), such as in the UV-C range, or in the UV-B range. In an embodiment, the light may be non-ionizing light. For example, in an embodiment, the light is UV-A light, which is non-ionizing. The wavelength may be in a range of, for example, 1 nm to 450 nm, 390 nm to 420 nm, 390 nm to 410 nm, 400 nm to 420 nm, or 400 nm to 410 nm. Using a non-ionizing light avoids ionizing irritation of the microbial biomass and can allow the end product to be labelled as organic food. With a black light wavelength (e.g., UV-A light), the liquid in which the biomass is suspended does not need to be alkaline. Carbon dioxide does not need to be suppressed or eliminated when a black light wavelength is used compared to a white light wavelength. In an embodiment, CO2 may be present in the suspension. The method may be performed without the addition of heat or the addition of adsorbants to the suspension. Additionally, using UV light compared to white light requires less energy.

Parameters of the light other than wavelength can vary. In various embodiments, the wattage can be in a range of 100 W to 1,000,000 W, 100 W to 500,000 W, 100 W to 100,000 W. 100 W to 50,000 W, 100 W to 10,000 W, or 100 W to 1,000 W. For example, the wattage can be 1000 W. The photon flux may also vary. In various embodiments, the photon flux may be in a range of 100 $\mu mol/(m^2 \cdot s)$ to 100,000 $\mu mol/(m^2 \cdot s)$, 100 $\mu mol/(m^2 \cdot s)$ to 50,000 $\mu mol/(m^2 \cdot s)$, 100 $\mu mol/(m^2 \cdot s)$ to 10,000 $\mu mol/(m^2 \cdot s)$, 100 $\mu mol/(m^2 \cdot s)$ to 5,000 $\mu mol/(m^2 \cdot s)$, 100 $\mu mol/(m^2 \cdot s)$ to 1500 $\mu mol/(m^2 \cdot s)$, 100 $\mu mol/(m^2 \cdot s)$ to 1000 $\mu mol/(m^2 \cdot s)$, 100 $\mu mol/(m^2 \cdot s)$ to 750 $\mu mol/(m^2 \cdot s)$, 100 $\mu mol/(m^2 \cdot s)$ to 500 $\mu mol/(m^2 \cdot s)$, 100 $\mu mol/(m^2 \cdot s)$ to 200 $\mu mol/(m^2 \cdot s)$, 4,000 $\mu mol/(m^2 \cdot s)$ to 100,000 $\mu mol/(m^2 \cdot s)$, or 10,000 $\mu mol/(m^2 \cdot s)$ to 100,000 $\mu mol/(m^2 \cdot s)$. The photon flux may also be greater than 100,000 $\mu mol/(m^2 \cdot s)$.

The length of time that the suspension is exposed to the light may vary. For example, the suspension can be exposed to the light for a period of minutes to days. In some embodiments, the exposure time may be less than 1 hour, 1 minute to 1 hour. 1 minute to 8 hours, 1 minute to 1 day, 1 minute to 10 days, about 1 minute, about 10 minutes, about 1 hour. 1 hour to 3 hours, 1 hour to 1 day, about 1 day, 1 day to 10 days, or about 10 days. Additionally, the suspension may be alternated between a light and dark environment.

In various embodiments, the treatment process may also include applying heat to the microbial biomass. In various embodiments, the source of the heat may be the lights, an external heat source, or a combination thereof. In an example embodiment, the temperature of the suspension may be in a range of 40° C. to 60° C. In an embodiment, the suspension may initially be at room temperature, and, during application of light, the temperature may be raised to be in a range of 40° C. to 60° C. and maintained at that temperature during the remainder of the application of the light. In various embodiments, the heat may be applied simultaneously or separately from the light.

Various embodiments can include growing and harvesting the microbial biomass, for example, in fermenters, open raceway ponds, photobioreactors, or biofilm-based systems, such as a revolving algal biofilm (RAB) photobioreactor.

Example growth and harvesting systems are described in International Patent Application Publication No. WO2014/153211, the disclosure of which is incorporated herein in its entirety. Referring again to FIG. 1, an example embodiment includes a fermentation system 20 in which biomass is grown. The fermentation system 20 can include a feed stock reservoir 22 and a fermenter 24. The feed stock reservoir 22 can include an inlet 26 and outlet 28. A microbial growth medium including, for example, a carbon source, a nitrogen source, a phosphorus source, and micronutrients, may be provided through the inlet 26 of the feed stock reservoir 22. The outlet 28 of the feed stock reservoir 22 may be fluidically coupled to an inlet 30 of the fermenter 24. The size of the fermenter 24 can vary significantly based on the application. For example, the size of the fermenter 24 can be in a range of, for example, 5 L to 100 L, such as about 50 L, or can be in the range of millions of gallons. The density of the liquid in the fermenter 24 may vary and can be, for example, 50 g/L. An outlet 32 of the fermenter 24 may be fluidically coupled to the treatment system 10.

As shown in FIG. 1, the treatment system 10 can include a pump 34 or any other suitable actuator or fluid control. The pump 34 can direct the suspension through the tubes 12. Similarly, in an example embodiment, the fermentation system 20 can include a pump 36 for directing the feed stock from the feed stock reservoir 22 to the fermenter 24. Either or both of the pumps 34, 36 can be an electric pump, a wheel, a paddlewheel, or can have any other suitable configuration to create any desirable flow pattern. It will be appreciated that the pumps 34, 36 can heat, cool, or otherwise adjust the conditions associated with the suspension or feed stock. It will also be appreciated that the pumps 34, 36 and any other suitable components can be associated with a computer, controller, or microcontroller that can be programmed to provide any suitable automated functionality.

Figure 3:
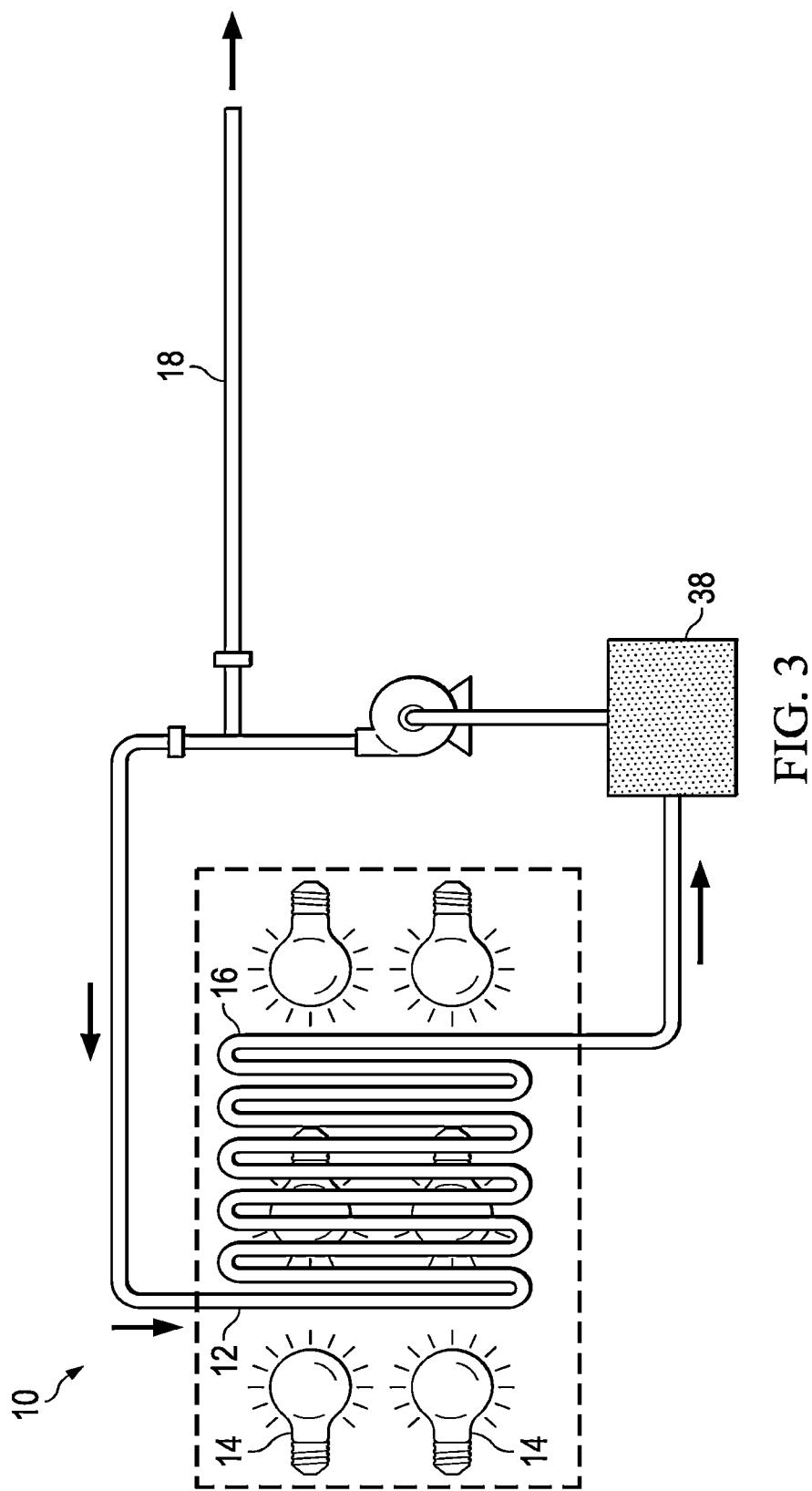
FIG. 3 depicts a schematic view of a treatment system according to an embodiment.

With reference to FIG. 3, in an embodiment, the treatment system 10 may include a reservoir 38 configured to contain a volume of the suspension. The tubes 12 may be fluidically coupled to the reservoir 38 such that the suspension can be recirculated from the reservoir 38 through the tubes 12. In an embodiment, the reservoir 38 may be opaque such that the suspension is in a dark environment while in the reservoir 38. An example configuration involving recirculation of the suspension may be considered a batch process, while an example configuration such as that in FIG. 1 may be considered a continuous process. In an embodiment, the treatment system 10 may be configured such that the suspension is exposed to the lights 14 for more time than it is contained in the reservoir 38.

It will be appreciated that any suitable microbial biomass, such as algae (including cyanobacteria), bacteria, or fungal strains, such as strains that can be used in food production, animal feed production, or food or feed supplement production can be used. Such strains can include *Chlorella* sp. (e.g., *Chlorella pyrenoidosa*), *Chlamydomonas* sp., *Botryococcus* sp. (e.g., *Botryococcus braunii*), *Phaeodactylum* sp., *Thalassiosira* sp., *Nannochloropsis*, sp., or *Isochrysis* sp. In an embodiment, the fermenter 24 is batch fed with 5-sporulation medium. Prior to the treatment process, the microbial biomass can be live or, for example, frozen. Any suitable parameter, such as the light intensity, light wavelength, exposure time, etc., can be optimized for any suitable species. It will be appreciated that the listed genus and species are described by way of example and additions and combinations are contemplated. Further, the biomass may be non-microbial. For example, the biomass may include plant material, protein, meat, or other food ingredients. The biomass may include a combination of materials (e.g., microbial, and non-microbial).

The treated biomass has reduced color, taste, and smell compared to the microbial biomass prior to the treatment process. For example, the initial color of the microbial biomass may be green, and the bleached color may be a light brown or white color. The bleached color may be similar to a wheat flour color. The change in color can be measured using, for example, a colorimeter. The change in color coordinates may be measured to determine the extent of the color change due to the bleaching process. In an example embodiment, L*a*b* coordinates may be used. For the red/green coordinate (a*), "a−", or a negative value for a* represents a green color, and "a+", or a positive value for a* represents a red color. In various embodiments, the a* coordinate of the treated color may be in a range of −2 to −0.5. In various embodiments, the a* coordinate of the treated color may be in a range of −0.2 to 0.2, or −0.1 to 0.2, or −0.1 to 0.1, or can be about −0.1, about zero, or zero. Example methods of quantifying color and a change in color may be found in: Pedreschi et al., "Development of a computer vision system to measure the color of potato chips," Food Research International, Volume 39, Issue 10, 2006, pages 1092-1098, https://doi.org/10.1016/j.foodres.2006.03.009; Yam et al., "A simple digital imaging method for measuring and analyzing color of food surfaces," Journal of Food Engineering, Volume 61, Issue 1, 2004, pages 137-142, https://doi.org/10.1016/80260-8774(03)00195-X; and Nakamura et al. "Analysis of the color change in fish during the grilling process," Food Science and Technology Research. 17:6, 2011, pages 471-478, each of which is incorporated herein by reference in its entirety.

The initial odor may be strong or fishy, and the odor after the treatment may be less noticeable. In an embodiment, the odor may be determined using an olfactometer and olfactometric analysis. Some compounds that cause a "fishy" odor can include geosmin (trans-1,10-dimethyl-trans-9-decalol) and MIB (2-methylisoborneol). Example methods of quantifying color and a change in color may be found in: Shinoda et al., "Using SPME-GC/REMPI-TOFMS to measure the volatile odor-active compounds in freshly cooked rice," ACS omega, 5.32, 2020, pages 20638-20642; Najib et al, "Fish quality study using odor-profile case-based reasoning (CBR) classification technique," ARPN Journal of Engineering and Applied Sciences, 11.10, 2016, pages 1-6; Wise et al, "Quantification of odor quality." Chemical senses, 25.4, 2000, pages 429-443; and Qin et al., "Changes in aroma profile of shiitake mushroom (*Lentinus edodes*) during different stages of hot air drying," Foods, 9.4, 2020, 444, each of which is incorporated herein by reference in its entirety. The treated biomass may have a protein content greater than 50%, such as in a range of 50% to 80%, 60% to 80%, or 60% to 70%, or about 64%. The treated biomass may have a carbohydrate content in a range of 5% to 30%, or about 23%. The treated biomass may have a lipid content in a range of 5% to 25%, or about 10%. The treated biomass may also include minerals, salts, and metals. Additionally, the treatment may result in sterilization or disinfection of the biomass. For example, the light treatment may kill microbes in the biomass that would be harmful or unwanted when the treated biomass is consumed.

Figure 4:
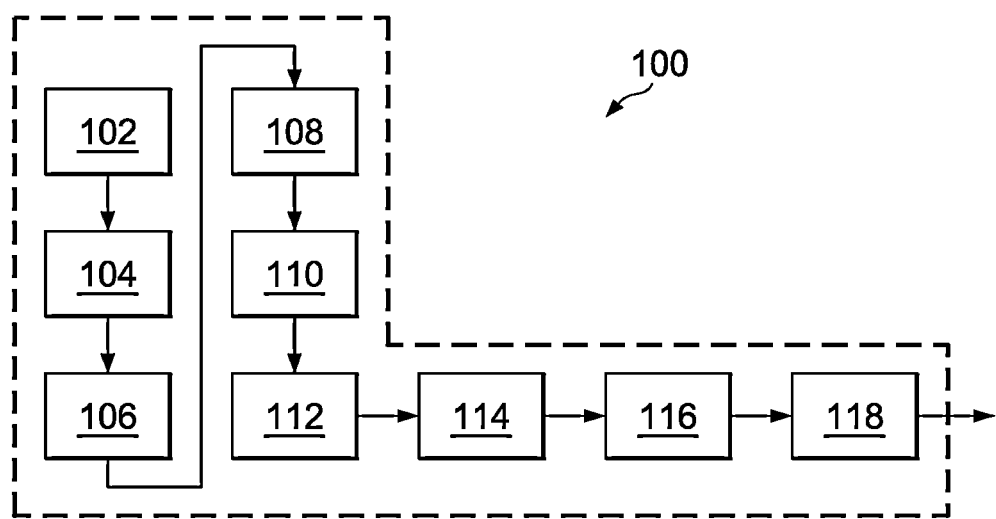
FIG. 4 depicts an example method of growing and treating biomass according to an embodiment where the biomass is in a suspension during treatment.

Now referring to FIG. 4, an example method 100 of growing algae and treating algae in a suspension according to an embodiment is shown. Algae seeds are prepared 102 for use in high-density fermentation 104. After the fermentation process 104 is complete, the green algae is concentrated or separated 106 from the fermentation liquid. The green algae cells are then suspended 108. As described above, examples of the suspension liquid include, without limitation, water, a microbial growth medium, or a microbial growth broth. The algae suspension can then be subjected to a treatment process 110 (e.g., using treatment system 10) in which the algae cells are bleached. The bleached algae cells can be concentrated 112. A lysing step or process 114 can be included in an embodiment where the treatment system does not cause cell lysing or as an additional step to ensure all or substantially all of the cells are lysed. The bleached algae can then be dried and optionally characterized 116 (e.g., for quality assurance or control or for designating the algae for certain uses or applications). The bleached algae can then be packaged and stored or shipped 118.

While the above description is directed towards treating microbial biomass in a suspension, the technology is not so limited. In some embodiments, the microbial biomass can be in a dry powder form during treatment. The dry biomass could be mixed or agitated during treatment to help ensure the biomass is evenly or uniformly treated. In an embodiment, the dry biomass could be mixed using pneumatic techniques, which could also be used to transport the dry biomass through the treatment system. Because of the reduced treatment volume of the dry biomass compared to biomass in suspension, the treatment time of the dry biomass may be reduced.

Figure 5:
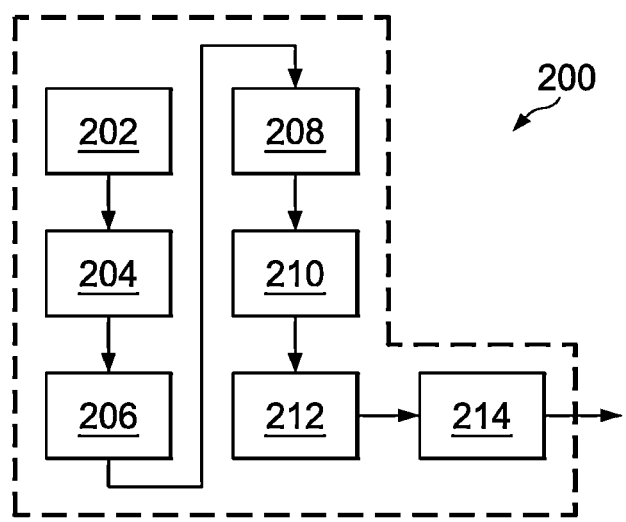
FIG. 5 depicts an example method of growing and treating biomass according to an embodiment where the biomass is dry during treatment.

Referring to FIG. 5, an example method 200 of growing algae and treating algae in a dry form according to an embodiment is shown. As discussed above, algae seeds can be prepared 202 for use in high-density fermentation 204. After the fermentation process 204 is complete, the green algae is concentrated or separated 206 from the fermentation liquid. In an embodiment, the green algae can undergo a lysing process 208 before the bleaching treatment. The green algae can then be dried 210 to be in a powder form. The dry green algae can then be subjected to a treatment process 212 (e.g., using treatment system 10) in which the algae cells are bleached. In an embodiment, the dry powder can be pneumatically moved through the treatment process using air. The bleached algae can then be packaged and stored or shipped 214. Although methods 100, 200 are described in relation to growing and treating algae, other types of biomass may be used in the methods described herein.

While the embodiments described above are directed towards microbial biomass, the technology is not so limited. In some embodiments, the bleaching processes and systems described herein may be used to treat plant biomass.

The present disclosure can be further understood by reference to examples, of which summaries and detailed descriptions follow. These examples are provided by way of illustration and are not meant to be limiting.

Example 1

Testing was conducted to determine whether light could be used to bleach microalgae. The starting material was *Chlorella* ATCC 53170, and the medium was ATCC 5 Sporulation. The microalgae was subjected to 10 days of light (Sample 1) and 1 day of light (Sample 2), and no light (Control Sample). The test samples were placed in glass tubes with a 1.75 cm outer diameter. Sample 1 was exposed to white light with a photon flux of 100 to 200 $\mu mol/(m^2 \cdot s)$ for 10 days and turned white. Sample 2 was exposed to light with a photon flux of 740 $\mu mol/(m^2 \cdot s)$ for 1 day and turned white. Samples 1 and 2 were shaken continuously at a rate of 120 rpm on an orbital shaker. A Control Sample was kept under dark conditions in an enclosed incubator and remained a green color.

Example 2

Testing was conducted using various wavelengths including: UV light, blue light, white light (e.g., full-spectrum lights), green light, and red light. The starting material was *Chlorella* ATCC 53170, and the medium was ATCC 5 Sporulation. The test samples were placed in glass tubes with a 1.75 cm outer diameter. The test samples were exposed to the various lights with a photon flux of 10,000 $\mu mol/(m^2 \cdot s)$ for a time of 2 hours. The test samples were shaken continuously at a rate of 120 rpm on an orbital shaker.

Results: The following types of light are ordered from the strongest bleaching effect (analyzed visually) to the least strong bleaching effect: UV light>Blue>White>Green>Red. Especially, using UV lights can decrease the total bleaching time to 0.5 hrs given the same bleaching setting. The results indicated that the higher frequency of the light used in bleaching, the better the bleaching effect was.

Example 3

A lab-scale bleaching test was performed. The starting material was *Chlorella pyrenoidosa* ATCC 53170, and the medium was ATCC 5 Sporulation. The algae seed was inoculated into a 250-ml Erlenmeyer flask with 100-ml of modified ATCC 5 Sporulation medium. The inoculation rate was set at 5%. The key parameters for modified ATCC 5 sporulation medium are: 20 g/L glucose and 8:1 C/N ratio for Culture 1 and 30 g/L glucose and 10:1 C/N ratio for Culture 2. The algae were cultured in the dark at 28° C. for 10 days prior to harvesting. The flasks were put on an orbital shaker with a shaking rate of 120 rpm. The cell density upon harvesting was about 8 to $10 \times 10^8$ cell/ml.

The algal cells were harvested via centrifuge at 5000 rpm for 10 min. The harvested algal pastes were resuspended by 1 g/L glucose solution prior to the cell bleaching process. After cell suspension, the cell density was about 2.7 to $3.3 \times 10^8$ cell/ml.

The solution containing resuspended algal cells was put under strong white light for 1-hr bleaching. The light intensity was kept at 5,000 $\mu mol/(m^2 \cdot s)$. The whole bleaching system was set on an orbital shaker with a shaking rate of 120 rpm. The temperature of the algal cell solution increased to and remained at 50° C. during the whole bleaching procedure. The resulting cells included 64% protein, 23% carbohydrates, 10% lipids, and 3% ashes.

In various embodiments disclosed herein, a single component can be replaced by multiple components and multiple components can be replaced by a single component to perform a given function or functions. Except where such substitution would not be operative, such substitution is within the intended scope of the embodiments.

Some of the figures can include a flow diagram. Although such figures can include a particular logic flow, it can be appreciated that the logic flow merely provides an exemplary implementation of the general functionality. Further, the logic flow does not necessarily have to be executed in the order presented unless otherwise indicated. In addition, the logic flow can be implemented by a hardware element, a software element executed by a computer, a firmware element embedded in hardware, or any combination thereof.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described in order to best illustrate principles of various embodiments as are suited to particular uses contemplated. The scope is, of course, not limited to the examples set forth herein, but can be employed in any number of applications and equivalent devices by those of ordinary skill in the art. Rather it is hereby intended the scope of the invention to be defined by the claims appended hereto.

What is claimed is:

1. A method of treating biomass, the method comprising:
mixing the biomass in a liquid to form a suspension; and
exposing the suspension to non-ionizing UV light to lyse the biomass to form treated biomass, wherein the temperature of the suspension reaches between 40° C. and 60° C. during the step of exposing, wherein the treated biomass has a lipid content of between 5% and 15%; and
including the treated biomass as at least a portion of a food product.

2. The method of claim 1, wherein the biomass comprises microbes, plant material, meat, or a combination thereof.

3. The method of claim 1, wherein the biomass has an initial odor, and the treated biomass has a treated odor, the initial odor being stronger than the treated odor.

4. The method of claim 1, wherein the biomass has an initial color, and the treated biomass has a treated color, the treated color being lighter than the initial color.

5. The method of claim 1, wherein the biomass has an initial taste, and the treated biomass has a treated taste, the initial taste being stronger than the treated taste.

6. The method of claim 1, further comprising heating the suspension.

7. The method of claim 1, further comprising:
growing the biomass; and
harvesting the biomass,
wherein the step of exposing the suspension to non-ionizing UV light to form treated biomass occurs after harvesting the biomass.

8. The method of claim 1, further comprising separating the treated biomass from the suspension.

9. The method of claim 8, further comprising drying the treated biomass after separating the treated biomass from the suspension.

10. The method of claim 9, further comprising packaging the treated biomass after separating the treated biomass from the suspension.

11. The method of claim 1, wherein the non-ionizing UV light is UV-A light.

12. The method of claim 1, wherein the non-ionizing UV light is UV-C light.

13. The method of claim 1, wherein the non-ionizing UV light is near UV light.

14. The method of claim 1, wherein a photon flux of the non-ionizing UV light is in a range of 100 µmol/(m²·s) to 100,000 µmol/(m²·s).

15. The method of claim 1, wherein exposing the suspension to the non-ionizing UV light kills cells in the suspension.

16. The method of claim 1, wherein the suspension is exposed to the non-ionizing UV light for a time of 1 minute to 10 days.

17. The method of claim 1, wherein the biomass is live biomass.

18. A method of producing treated microbial biomass, the method comprising:
growing microbial biomass;
harvesting the microbial biomass;
mixing the microbial biomass in a liquid to form a suspension;
exposing the suspension to non-ionizing UV light to lyse the microbial biomass to form the treated microbial biomass, wherein the temperature of the suspension reaches between 40° C. and 60° C. during the step of exposing, and wherein the treated biomass has a lipid content of between 5% and 15%;
separating the treated microbial biomass from the suspension; and
packaging the treated microbial biomass.

19. The method of claim 18, wherein the microbial biomass is microalgae, and wherein growing the microbial biomass comprises growing the microalgae using fermentation.

20. The method of claim 18, wherein the microbial biomass in the suspension is live when exposed to the non-ionizing UV light.

* * * * *